United States Patent [19]

Blum et al.

[11] Patent Number: 4,748,140

[45] Date of Patent: May 31, 1988

[54] IN SITU ACTIVATION PROCESS FOR FLUID BED OXIDATION CATALYSTS

[75] Inventors: Patricia R. Blum, Macedonia; Ernest C. Milberger, Solon; Mark L. Nicholas, Cleveland; Patricia A. Zock, Maple Hts., all of Ohio

[73] Assignee: The Standard Oil Company, Cleveland, Ohio

[21] Appl. No.: 685,437

[22] Filed: Dec. 24, 1984

Related U.S. Application Data

[63] Continuation of Ser. No. 550,276, Nov. 9, 1983, abandoned, which is a continuation of Ser. No. 334,693, Dec. 28, 1981, abandoned.

[51] Int. Cl.$^4$ .............................................. B01J 27/198
[52] U.S. Cl. ..................................... 502/209; 549/258; 549/259; 549/260
[58] Field of Search .......................................... 502/209

[56] References Cited

U.S. PATENT DOCUMENTS

| | | | |
|---|---|---|---|
| 3,156,706 | 11/1964 | Kerr | 260/346.8 |
| 3,907,833 | 9/1975 | Slinkard et al. | 260/346.8 |
| 3,915,892 | 10/1975 | Harrison | 252/435 |
| 3,932,305 | 1/1976 | Jurewicz et al. | 252/429 R |
| 3,977,998 | 8/1976 | Freerks et al. | 252/435 |
| 3,985,775 | 10/1976 | Harrison | 260/346.8 A |
| 4,013,586 | 3/1977 | Dolan et al. | 252/437 |
| 4,092,269 | 5/1978 | Mount et al. | 252/435 |
| 4,094,888 | 6/1978 | Straus | 260/346.75 |
| 4,111,963 | 9/1978 | Mount et al. | 260/346.75 |
| 4,122,096 | 10/1978 | Bertolacini et al. | 260/346.75 |
| 4,132,670 | 1/1979 | Katsumoto et al. | 252/437 |
| 4,171,316 | 10/1979 | Pedersen | 260/346.75 |
| 4,178,298 | 12/1979 | Stefani et al. | 260/346.75 |
| 4,181,628 | 1/1980 | Stefani et al. | 252/435 |
| 4,187,235 | 2/1980 | Katsumoto et al. | 260/346.75 |
| 4,202,798 | 5/1980 | Johnson et al. | 252/435 X |
| 4,209,423 | 6/1980 | Hutchings et al. | 252/437 X |
| 4,222,945 | 9/1980 | Higgins et al. | 252/437 X |

FOREIGN PATENT DOCUMENTS

7314746 10/1973 Netherlands .

OTHER PUBLICATIONS

Chem. Abst. 93 149763d, UPO Cat. for Oxide of Butane, Zozhigahov, vol. 93, 1980, p. 675.

Primary Examiner—Helen M. S. Sneed
Assistant Examiner—William G. Wright
Attorney, Agent, or Firm—D. P. Yusko; D. J. Untener; L. W. Evans

[57] ABSTRACT

A process for activating fluid bed catalysts useful for producing maleic anhydride from 4 carbon atom hydrocarbons is provided including contacting the fluidized catalyst containing the mixed oxides of vanadium and phosphorus with oxygen and a reducing gas at least partially combustible with oxygen at elevated temperatures sufficient to cause such combustion, wherein the molar ratio of reducing gas to oxygen is greater than the stoichiometric ratio required for complete combustion of the reducing gas. Also provided are catalysts activated by the process of the invention, as well as a process for producing maleic anhydride utilizing the catalysts thus activated.

9 Claims, No Drawings

IN SITU ACTIVATION PROCESS FOR FLUID BED OXIDATION CATALYSTS

REFERENCES TO RELATED APPLICATIONS

This is a continuation application of application U.S. Ser. No. 550,276, filed Nov. 9, 1983, now abandoned, which was a continuation of application U.S. Ser. No. 334,693, filed Dec. 28, 1981, now abandoned.

BACKGROUND OF THE INVENTION

The present invention relates to the activation of fluid bed oxidation catalysts. More particularly the present invention relates to the activiation of fluid bed oxidation catalysts useful in the preparation of maleic anhydride from 4-carbon atom hydrocarbons, including n-butane.

Oxidation catalysts containing the mixed oxides of vanadium and phosphorus have been utilized to produce maleic anhydride from 4-carbon atom hydrocarbons, such as n-butane. Methods have been investigated for activating, or increasing the catalytic activity of these catalysts. It is taught in the literature to "condition" vanadium phosphate-containing maleic anhydride catalysts under the flow of a low level of hydrocarbon in air, such as 0.2 volume percent to 2 volume percent hydrocarbon in air at temperatures of 300° C. to 600° C., as in U.S. Pat. No. 4,171,316.

U.S. Pat. No. 4,122,096 teaches conditioning of a dehydrated catalyst precursor with CO, $H_2$ or $H_2S$ in the absence of oxygen, at a temperature of from 300° C. to 600° C.

U.S. Pat. Nos. 4,178,298 and 4,181,628 discuss activating a mixed vanadium and phosphorus oxide catalyst at temperature of 300° C. to 500° C. by passing over the catalyst, a gaseous hydrocarbon component having 2 to 6 carbon atoms with the exclusion of molecular oxygen.

Attempting to "condition" a fluid bed catalyst with low levels of hydrocarbon in air under normal operating conditions has been found to have little beneficial effect. Further, it is impractical and nearly impossible to utilize an in-reactor activation method in a fluid bed reactor which comprises contacting the fluidized catalyst with a hydrocarbon at high temperature in the absence of molecular oxygen. Commercial fluid bed reactors do not contain means for heating the catalyst bed and gas stream to the temperatures required to achieve the desired activation utilizing oxygen-free hydrocarbon feeds. The requisite external heating mode of operation is not desired for fluid bed reactions, and indeed fluid bed processes are attractive for the reason that such external heating means are not required for normal operation.

Where it is desired to activate catalysts containing the mixed oxides of vanadium and phosphorus for the partial oxidation of n-butane to form maleic anhydride, the activation of the catalyst with the hydrocarbon n-butane in the absence of oxygen would be extremely expensive, with regard to the volume of butane required to "fluidize" the catalyst bed. Further, stringent safety precautions would also be required to insure that no explosive mixtures of air/butane result outside the reactor.

Aside from economic and mechanical considerations, it is thought that contacting the vanadium phosphorus mixed oxide catalyst with reducing gases, including hydrocarbons, in the absence of oxygen merely causes reduction of the catalyst components (particularly vanadium) by extracting lattice oxygen, causing the catalyst crystallite structure to reach a static configuration. Oxygen atoms are thus depleted from the catalytic active sites, and are unavailable for reaction with hydrocarbon reactants to yield useful product. While this procedure may enhance the activity of catalysts that were initially over-oxidized, the overall effect upon catalysts having a proper component valence range could be detrimental over time by inducing change to the static configuration.

SUMMARY OF THE INVENTION

It is therefore an object of the present invention to achieve in situ activation of fluid bed maleic anhydride catalysts containing the mixed oxides of vanadium and phosphorus.

We have found that fluid bed maleic anhydride catalysts containing the mixed oxides of vanadium and phosphorus can be activated in situ (in the fluid bed reactor) by contacting the fluidized catalyst with oxygen and a reducing gas at least partially combustible with oxygen at an elevated temperature sufficient to cause such combustion.

Although it is not intended that the scope of this invention be limited to theory, it is thought that the contacting of the catalyst, while fluidized, with both oxygen and a reducing gas at least partially combustible with oxygen at an elevated temperature sufficient to cause such combustion provides a more effective, dynamic activation of the catalyst. In contrast to the static extraction of oxygen from the catalyst to provide reduction as in the prior art, when oxygen is present together with the combustible reducing gas as in the process of the present invention, at elevated temperature, the catalyst is induced to operate catalytically, and a dynamic, interactive catalytic activation process results. The catalyst is permitted to take up oxygen as well as yield oxygen to the reducing feed component, allowing the active site and catalyst microcrystalline structure to undergo dynamic reorientation. This is thought to result in localized crystalline phase changes which optimize the catalyst activity.

Because the activation procedure is carried out at temperatures sufficient to cause at least partial combustion of the reducing gas, the required activation temperature is attained by the heat of combustion after initial startup heating by conventional fluid bed preheaters.

The fact that partial combustion takes place in the fluidized bed lessens the concentration of heated combustible reducing gas in the effluent stream, such reducing gas being diluted by the combustion products, although precautions should still be taken to insure that an explosive mixture is not permitted to develop downstream of the reactor. The presence of the combustion product diluents, such as $H_2O$ if $H_2$ is utilized as the reducing gas, $H_2O$ and $SO_2$ if $H_2S$ is utilized as the reducing gas, and $H_2O$ and $CO_2$ if hydrocarbon is utilized as the reducing gas, decreases the concentration of combustible gas in the effluent. The activating feed of the present invention, utilizing air in addition to reducing gas, is also less costly.

In general, the process of the present invention includes activating a fluid bed catalyst by contacting a fluidized catalyst containing the mixed oxides of vanadium and phosphorus with oxygen and a reducing gas at least partially combustible with oxygen at an elevated temperature sufficient to cause combustion, wherein the molar ratio of reducing gas to oxygen is greater than the stoichiometric ratio required for complete combustion of the reducing gas.

The present invention further provides a fluidizable catalyst containing the mixed oxides of vanadium and phosphorus, activated by the above process.

The present invention further provides a process for producing maleic anhydride, utilizing the activated catalyst prepared by the above process.

DETAILED DESCRIPTION OF THE INVENTION

Catalysts for the production of maleic anhydride from 4-carbon atom hydrocarbons, such as n-butane, butenes, and butadiene, particularly n-butane, generally contain the mixed oxides of vanadium and phosphorus. The catalysts may additionally contain promoter elements, including but not limited to alkali or alkaline earth metals, titanium, zirconium, hafnium, niobium, molybdenum, iron, cobalt, nickel, copper, zinc, cadmium, rare earths, cerium, uranium and mixtures thereof. The molar ratio of promoter elements to vanadium is generally 0.001:1 to 1:1, preferably about 0.1:1 to 0.5:1. The molar ratio of phosphorus to vanadium is generally about 0.5:1 to about 2:1, preferably about 0.9:1 to about 1.6:1. The valence of the vanadium component of the catalyst is generally reduced from the pentavalent state, the valence of vanadium generally being between about 3.5 to about 4.6 and preferably being about 4. The maleic anhydride catalyst may additionally contain diluents or supports, such as titania, alumina, alumina-silica, zirconia, silica, silicon carbide, and the like.

The catalysts may be prepared by reacting catalyst component containing compounds in the presence or absence of a corrosive reducing agent in a liquid, including but not limited to water, alcohols, aldehydes, glycols, ketones, halogenated olefins, and the like. Suitable corrosive reducing agents to provide vanadium in the proper valence state include but are not limited to HCl, HBr, and oxalic acid. Suitable liquid media capable of reducing vanadium to its proper valence state include but are not limited to isopropanol, isobutanol, crotyl alcohol, allyl alcohol, isopentanol, acetaldehyde, propionaldehyde, butyraldehyde, ethylene glycol, methyl ethyl ketone, perchloropropene, hexachlorobutadiene and the like.

Suitable vanadium compounds for use in preparing the maleic anhydride catalysts include vanadium pentoxide or vanadium salts, such as ammonium metavanadate and vanadium oxytrihalides. Suitable phosphorus containing compounds include phosphoric acid, including metaphosphoric acid, orthophosphoric acid, triphosphoric acid and pyrophosphoric acid, and phosphorus pentoxide, phosphorus oxyiodide, phosphorus oxychloride, phosphorus pentachloride, and the like. Suitable promoter element containing compounds include promoter metal oxides, hydroxides, nitrates, halides, or salts of organic acids such as acetates, formates, butyrates, benzylates, and the like.

The catalyst components are mixed in the liquid medium, before or after the vanadium component is reduced to its proper valence state. The catalyst precursor formed is recovered and dried. The catalyst is formed into fluid bed form by crushing and screening the catalyst particles to a proper size, such as in the range of about 20 to about 300 microns, by the oil drop method, wherein an aqueous solution or slurry of the catalyst is dropped into a heated oil bath to form solid particles, or by spray drying to form the desired particles. The catalyst may be calcined before or after forming into the fluidizable particles, dependent upon the method of preparation chosen. A method of preparing fluidizable catalysts useful for the production of maleic anhydride from 4-carbon atom hydrocarbons such as n-butane is disclosed in U.S. Ser. No. 220,624 assigned to our common assignee, incorporated herein by reference. The specific method of preparing the catalysts to be activated is not, however, critical to the process of the present invention.

Hydrocarbons reacted to form maleic anhydride include n-butane, n-butenes, 1,3 butadiene, or a mixture thereof. The molecular oxygen used in the reaction is most conveniently added as air, but synthetic streams containing molecular oxygen are also suitable. In addition to the hydrocarbon and molecular oxygen, other gases may be added to the reactant feed, such as steam or nitrogen. Preferably, oxygen/hydrocarbon ratios in the reactor feed are about 4 to about 20 moles of oxygen per mole of hydrocarbon.

The reaction temperature may vary widely and is dependent upon the particular hydrocarbon and catalyst employed. Temperatures of about 325° C. to about 500° C. are preferred. The reaction may be conducted at atmospheric, super atmospheric or subatmospheric pressure, although operation at superatmospheric pressure is preferred.

CATALYST ACTIVATION

Although it has been disclosed that maleic anhydride catalysts containing the mixed oxides of vanadium and phosphorus can be activated by contacting the catalyst in the absence of molecular oxygen with gaseous hydrocarbons or reducing agents such as hydrogen or hydrogen sulfide, such activation can be utilized for fixed bed catalyst forms, and as explained above, cannot readily be utilized as an in situ activation for fluidizable catalysts in a fluid bed reactor.

In the process of the present invention, fluidizable catalysts containing the mixed oxides of vanadium and phosphorus are activated by contacting the catalyst with oxygen and a reducing gas at least partially combustible with oxygen at an elevated temperature sufficient to cause such combustion, in a molar ratio of reducing gas to oxygen greater than the stoichiometric ratio required for complete combustion.

Suitable reducing gases include the hydrocarbon being utilized as a reactant to provide maleic anhydride, such as n-butane, n-butenes, and butadiene although other hydrocarbons are also suitable. Such other hydrocarbons may have up to 10 carbon atoms and may include methane, ethane, propane, isobutane, isobutylene, pentane, hexane, benzene and the like. Other suitable reducing agents include hydrogen, ammonia, carbon monoxide, hydrogen sulfide, and the like.

Oxygen may be added as air or synthetic streams containing molecular oxygen may be utilized. Inert gases may be added to the activating feed, including but not limited to nitrogen, argon, carbon dioxide, steam, and the like.

The molar ratio of reducing gas to oxygen in the activation feed stream is about 10:1 to about 1:3, preferably about 5:1 to about 1:2. If air is used as the source of oxygen, the molar ratio of reducing gas to air is about 2:1 to about 1:15, preferably about 1:1 to about 1:10. Inert gases in addition to those provided by air in the activation feed, may be added according to the process of the present invention. The amount of total inert gas to reducing gas may be between 0:1 to 50:1 or greater, although preferably the amount of inert gas added to the activation feed, in addition to the inerts provided by air, are added in the molar ratio of inerts to reducing gas of about 3:1 to about 30:1.

The activation procedure should be carried out at a temperature high enough to cause and sustain at least partial combustion of the reducing gas. The temperature required varies for different catalyst formulations, but can be determined by simple experimentation. Generally, the activation procedure is carried out at temperatures between about 400° C. and 550° C.

The time required for activation depends in part upon the degree of activation required and the temperature at which the activation is carried out. In general, higher activation temperatures and longer activation time, independently contribute to a more activated form of the catalyst. Activation may take place at subatmospheric, atmospheric or superatmospheric pressures.

Activating conditions can be reached by various methods. The change to and from activating temperature may be accomplished under reaction feeds, activating feeds, or an inert gas.

The activation procedure according to the process of the present invention may be carried out in the fluid bed reactor at any time in the catalysts' life that activity is desired to be increased. It is preferred, however, that the activation procedure be carried out with catalyst that has operated to produce maleic anhydride from hydrocarbon. That is, the activation procedure seems to have a more beneficial effect upon catalyst in which active sites of catalytic activity have been established by working to catalyze the reaction of hydrocarbon, preferably n-butane, to maleic anhydride, in contrast to catalyst which has not yet been subjected to normal maleic anhydride producing conditions.

The products of the activation procedure are essentially the combustion products CO and $CO_2$, when hydrocarbons are utilized as a reducing gas. Even when n-butane is utilized as the reducing gas, during activation there is little or no maleic anhydride production. There is some hydrocarbon breakthrough, however, and this can be either recycled or disposed of in a catalytic incinerator, without permitting an explosive mixture of oxygen and heated hydrocarbon to form.

SPECIFIC EMBODIMENTS

EXAMPLE 1

A catalyst containing the mixed oxides of vanadium and phosphorus, having a phosphorus to vanadium ratio of 1.2:1 were prepared as described in U.S. Ser. No. 220,624, incorporated by reference above. The fluidizable catalyst was used to produce maleic anhydride from n-butane in a 440 cc fluid bed reactor consisting of about a 51 cm length of stainless steel tubing having an outer diameter of about 3.8 cm, having a stainless steel sparger at the bottom of the tube to act as a gas (air) distributor with an axial 0.64 cm outer diameter thermowell and a separate hydrocarbon inlet at the bottom of the tube. The reactor was fitted with internal gas redistributing baffles. Gas preheating and reactor temperature control was accomplished by placement of the reactor unit in a thermostatic fluidized sand bath.

Flasks for receiving the product maleic anhydride were air cooled, and tail gases were routed to a gas chromatograph for analysis. Reaction conditions and results of the tests run are described in the Table below. The throughput of hydrocarbon feed in the production of maleic anhydride, or the working rate imposed upon the catalyst can be described as WWH, or weight of feed/weight of catalyst/hour, being 0.05 WWH.

After the catalyst had been run for about 200 hours, achieving a molar yield of 51.4%, the activation feed of 1 mole butane to 1 mole air to 3 moles additional nitrogen was used to fluidize the catalyst bed at a temperature of 480° C. for 19.4 hours. After the activation procedure, reaction feeds of 1 mole of butane to 30 moles of air were resumed resulting in an increase of activity demonstrated by a 55.6% yield to maleic anhydride. Even after the reaction temperature was dropped 6° C. from the post activation run temperature of 421° C., the activity of the catalyst remained excellent, with a 55.0% yield of maleic anhydride. Reaction and activation conditions and results for example 1 and the following examples are contained in the Table below.

EXAMPLES 2-5

Catalysts were prepared according to the procedure of Example 1. The catalysts were used to produce maleic anhydride by n-butane oxidation, and were subjected to the activation process of the present invention under varied times, temperatures, and activation feeds as set out in the Table below. After the activation had been carried out in each example, the catalysts exhibited a substantial increase in activity, demonstrated by a sizable increase in the yield of maleic anhydride. In Example 5, the catalyst underwent two successive activations, with a substantial increase in activity resulting after both activation procedures.

EXAMPLES 6-8

Vanadium, phosphorus mixed oxide containing catalysts were prepared by methods designed to produce catalytic material having lower activity than the catalysts prepared above, to determine whether the activation procedure of the present invention was useful in increasing the activity of low conversion catalysts. As reported in the Table below, in each Example, the activation procedure resulted in a substantial increase in catalytic activity. These catalysts were tested according to the run procedure of Example 1.

It is to be understood that the scope of the present invention is not to be limited by the above examples. Various butane/air/inert gas ratios may be utilized and have been demonstrated, such as 1/4/0 at 420° C. for 19 hours, 1/3/10 at 460° C. for 18 hours, and 1/5/15 at 480° C., among others.

The activation procedure may be carried out while the reactor is "on line" or operating, by changing the reaction feed to the activation feed and either maintaining or increasing temperature. It is also within the scope of the present invention that a slip stream be provided from the reactor to permit catalyst to be continuously withdrawn, subjected to the activation procedure in a continuous loop and reintroduced into the main reactor continuously while the reactor continues in operation. Such a procedure would permit the maintenance of a high level of activity in the reactor catalyst bed by continuously introducing freshly activated catalyst to the main catalyst bed.

It is also within the scope of the present invention to apply the activation feeds and procedures to fixed catalyst beds, although the process of the present invention is particularly suited to the activation of fluidized catalyst beds.

Thus it should be apparent to those skilled in the art that the subject invention accomplishes the objects set forth above. It is to be understood that the subject invention is not to be limited by the examples set forth herein. These have been provided merely to demonstrate operability, and the selection of methods of preparation of the vanadium and phosphorus mixed oxide containing catalysts, the hydrocarbon feedstocks, the activation feeds, reducing gases, molar ratios, and reaction and activation conditions can be determined from the total specification disclosure provided without departing from the spirit of the invention herein disclosed and described, the scope of the invention including equivalent embodiments, modifications and variations that fall within the scope of the attached claims.

TABLE

Activation/Operation of Vanadium Phosphorus Mixed Oxide Catalysts For N—Butane Oxidation to Maleic Anhydride Run Feed = 30 Air/1
WWH = 0.05

| Example No. Recovery Runs | Feed HC/Air/N$_2$ | Activation Temperature °C. | Time Hours | Run Temperature °C. | % Total Conversion | Maleic Anhydride % Yield | % Selectivity |
|---|---|---|---|---|---|---|---|
| Before | | | | 422 | 90.4 | 51.4 | 56.9 |
| 1. | 1/1/3 | 480 | 19.4 | | | | |
| After | | | | 421 | 94.2 | 55.6 | 59.1 |
| Before | | | | 420 | 87.9 | 49.2 | 56.0 |
| 2. | 1/10/15 | 460–472 | 19 | | | | |
| After | | | | 419 | 92.1 | 56.2 | 61 |
| Before | | | | 421 | 86.5 | 53.2 | 61.5 |
| 3. | 1/1/3 | 420 | 18 | | | | |
| After | | | | 420 | 90.8 | 57.7 | 63.5 |
| Before | | | | 420 | 87.6 | 50.8 | 58.0 |
| 4. | 1/1/3 | 500 | 2 | | | | |
| After | | | | 400 | 85.9 | 57.1 | 66.5 |
| Before 1st | | | | 419 | 86.0 | 52.1 | 60.5 |
| 5. | 1/1/3 | 460 | 19.2 | | | | |
| After 1st Before 2nd | | | | 419 | 89.4 | 55.7 | 62.5 |
| | 1/1/3 | 480 | 15.5 | | | | |
| After 2nd | | | | 420 | 92.4 | 58.5 | 63.3 |
| Before | | | | 421 | 60.3 | 41.2 | 70.2 |
| 6. | 1/1/3 | 460 | 5.2 | | | | |
| After | | | | 421 | 66.9 | 46.9 | 70.1 |
| Before | | | | 421 | 61.8 | 38.7 | 62.6 |
| 7. | 1/10/5.7 | 460 | 14.6 | | | | |
| After | | | | 419 | 68.3 | 43.7 | 64.1 |
| Before | | | | 421 | 50.7 | 29.5 | 58.2 |
| 8. | 1/1/3 | 500 | 16.5 | | | | |
| After | | | | 420 | 70.6 | 47.0 | 66.6 |

HC = n-butane greater than the stoichiometric ratio required for complete combustion of the reducing gas.

2. A process as in claim 1 wherein the ratio of reducing gas to oxygen is about 10:1 to about 1:3.

3. A process as in claim 1 wherein the ratio of reducing gas to oxygen is about 5:1 to about 1:2.

4. A process as in claim 1 wherein the catalyst is additionally contacted with an inert gas.

5. A process as in claim 1 wherein air is the source of oxygen.

6. A process as in claim 5 wherein the catalyst is contacted with an inert gas in addition to the inert gas contained in air.

7. A process as in claim 1 wherein the temperature is within a range of about 400° C. to about 550° C.

8. A process as in claim 1 wherein the reducing gas is selected from H$_2$, H$_2$S, CO, hydrocarbons having from 1 to about 10 carbon atoms, and mixtures thereof.

9. A process as in claim 1 wherein said catalyst additionally contains a promoter element selected from at least one of an alkali metal, an alkaline earth metal, titanium, zirconium, hafnium, niobium, molybdenum, iron, cobalt, nickel, molybdenum, iron, cobalt, copper, zinc, cadmium, cerium, rare earths, uranium and mixtures thereof.

We claim:

1. A process for activating a fluid bed catalyst by contacting a fluidized catalyst containing the mixed oxides of vanadium and phosphorus with oxygen and a reducing gas at least partially combustible with oxygen, the contacting conducted at an elevated temperature sufficient to cause combustion of the reducing gas, wherein the molar ratio of reducing gas to oxygen is

* * * * *